United States Patent
Glaser et al.

(10) Patent No.: US 12,170,144 B1
(45) Date of Patent: Dec. 17, 2024

(54) EQUIPMENT MEASURING AND TESTING SYSTEM FOR A MEDICAL FACILITY

(71) Applicants: Tamar Glaser, Palos Verdes, CA (US); Hannah Glaser, Palos Verdes, CA (US); Roberta Davis, Palos Verdes, CA (US)

(72) Inventors: Tamar Glaser, Palos Verdes, CA (US); Hannah Glaser, Palos Verdes, CA (US); Roberta Davis, Palos Verdes, CA (US)

(*) Notice: Subject to any disclaimer, the term of this patent is extended or adjusted under 35 U.S.C. 154(b) by 0 days.

(21) Appl. No.: 18/229,494

(22) Filed: Aug. 2, 2023

Related U.S. Application Data

(63) Continuation-in-part of application No. 17/712,185, filed on Apr. 4, 2022, now abandoned, which is a continuation of application No. 16/163,447, filed on Oct. 17, 2018, now abandoned.

(51) Int. Cl.
*G16H 40/40* (2018.01)
*G16H 40/20* (2018.01)
*G16H 40/67* (2018.01)

(52) U.S. Cl.
CPC .............. *G16H 40/40* (2018.01); *G16H 40/20* (2018.01); *G16H 40/67* (2018.01)

(58) Field of Classification Search
CPC ......... G16H 40/40; G16H 40/20; G16H 40/67
See application file for complete search history.

(56) References Cited

U.S. PATENT DOCUMENTS

| | | | |
|---|---|---|---|
| 2014/0095182 A1* | 4/2014 | Fletcher | G16H 40/20 705/2 |
| 2019/0309975 A1* | 10/2019 | Salem | F24F 11/64 |
| 2021/0007701 A1* | 1/2021 | Ten Cate | G16H 30/20 |
| 2021/0104319 A1* | 4/2021 | De Melo | G16H 40/63 |
| 2022/0230183 A1* | 7/2022 | Glaser | F24F 11/0008 |
| 2023/0266028 A1* | 8/2023 | Rogers | F24F 11/30 700/276 |

* cited by examiner

*Primary Examiner* — Mohammad Ali
*Assistant Examiner* — Sheela Rao
(74) *Attorney, Agent, or Firm* — Edmond DeFrank

(57) ABSTRACT

The embodiments disclose an equipment measuring and testing system for a medical facility including a plurality of sensors coupled to at least one medical device located in at least one operating room configured to measure operation performance levels to be within a predetermined range of compliance standards, a wireless communication device coupled to each sensor of the plurality of sensors configured to wirelessly transmit measured operation performance levels to a server, a server coupled to the plurality of sensors configured to determine if the at least one medical device is within the predetermined range of compliance standards and alert a user of a compliance status based on the determination, and a plurality of settings actuators coupled to the at least one medical device and the server configured to adjust settings of the at least one medical device to be within the predetermined range of compliance standards.

20 Claims, 16 Drawing Sheets

EQUIPMENT MEASURING AND TESTING SYSTEM FOR A MEDICAL FACILITY

BACKGROUND

Advances in the health care industry have been accelerated over the past decades at ever increasing rates. Diagnostics, treatments, and medical procedures have become more specialized covering a wide range of health conditions. Health care services have expanded for the benefit of the patients. Accreditation of health care centers has provided patients and the health care insurers with oversight into the quality of care. The numbers and depth of compliance investigation of health care oversight agencies have equally expanded at the same accelerated rate as the advances in the health care industry. The business of the health care industry companies is faced with keeping pace with the accelerated rate of changes in order to maintain a compliant status with the oversight accreditation standards and regulations. Greater numbers of equipment, systems, services and facilities covering the wide range of medical specialties and the broadening of the accreditation standards and regulations to match those advances can no longer be handled by a cadre of administrators and staff alone.

BRIEF SUMMARY OF THE INVENTION

In the present invention, an equipment measuring and testing system for a medical facility includes equipment operating performance measurements to comply with compliance standards. A measuring and testing control server is used to receive, process, and record sensor measurements of operational performance levels of, for example, operating room equipment. The operating room equipment includes for example a humidifier, an air flow ventilator, an air conditioner, and lights. The server is also used to receive, process, and record measurements of treatment room equipment. The treatment room equipment includes a humidifier, an air flow ventilator, and an air conditioner. The server is also used to receive, process, and record measurements of a procedure room, wherein the equipment includes a radiology x-ray machine, cardiology ECG devices, gynecological ultrasound devices, and gynecology sonogram devices.

The embodiments disclose an equipment measuring and testing system for a medical facility including a plurality of sensors coupled to at least one medical device located in at least one operating room used to measure operation performance levels to be within a predetermined range of compliance standards, a wireless communication device coupled to each sensor of the plurality of sensors used to wirelessly transmit measured operation performance levels to a server, a server coupled to the plurality of sensors used to determine if the at least one medical device is within the predetermined range of compliance standards and alert a user of a compliance status based on the determination, and a plurality of settings actuators coupled to the at least one medical device and the server used to adjust settings of the at least one medical device to be within the predetermined range of compliance standards.

DETAILED DESCRIPTION OF THE INVENTION

In the following description, reference is made to the accompanying drawings, which form a part hereof, and in which is shown by way of illustration a specific example in which the invention may be practiced. It is to be understood that other embodiments may be utilized and structural changes may be made without departing from the scope of the embodiments.

General Overview:

It should be noted that the descriptions that follow, for example, in terms of an equipment measuring and testing system for a health care facility are described for illustrative purposes and the underlying system can apply to any number and multiple types of health care companies and facilities. In one embodiment of the present invention, the equipment measuring and testing system for a medical facility is using digital sensors. The equipment measuring and testing system for a medical facility includes the use of optical scanners and remote digital actuators.

In one embodiment an equipment measuring and testing system for a medical facility includes a plurality of sensors coupled to equipment in at least one operating room. The plurality of sensors are used to measure an operation performance level of at least one air flow ventilator to determine if the at least one air flow ventilator is operating within a predetermined range of compliance standards. Also, sensor measured non-compliant performance data of an operating room piece of equipment including the at least one air flow ventilator generates an alert transmitted to a user.

A wireless communication device is also included and coupled to each sensor of the plurality of sensors and used to wirelessly transmit sensor measurements to a server. A server coupled to the plurality of sensors is used to process the sensor measurements to determine any operation performance level adjustment for each piece of equipment to operationally perform within the predetermined range operation performance level. A plurality of settings actuators coupled to each piece of equipment settings controls are used to adjust the piece of equipment operation performance ranges according to operating performance ranges meeting compliance standards ranges based on the adjustment instructions transmitted wirelessly from the server.

The abbreviation used herein "AAAHC" refers to the Accreditation Association for Ambulatory Health Care (AAAHC). The abbreviation used herein "AAAASF" refers to the American Association for Accreditation of Ambulatory Surgery Facilities (AAAASF).

Figure 1:
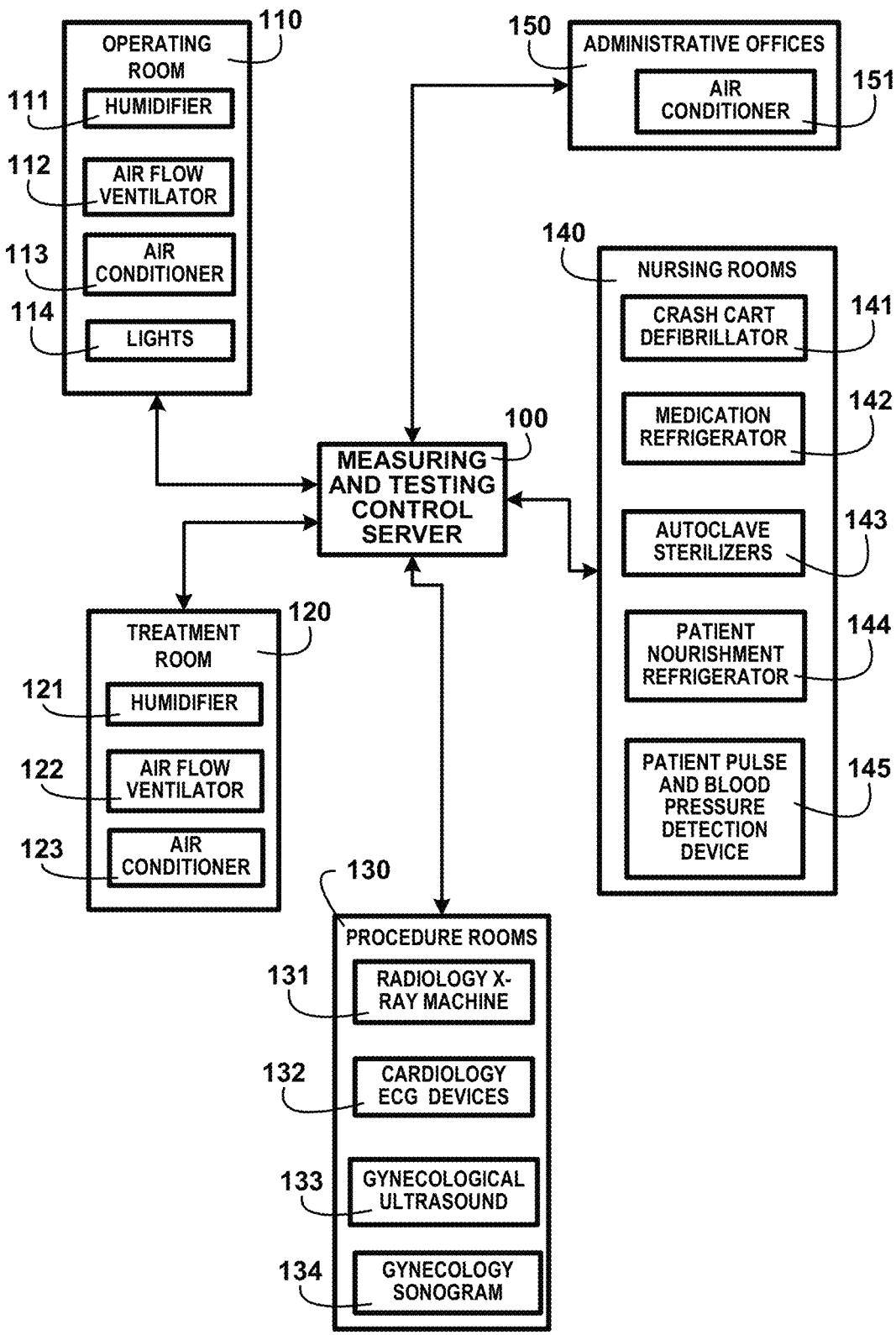
FIG. 1 shows for illustrative purposes only an example of an overview of facility equipment operating performance measurement of one embodiment.

FIG. 1 shows for illustrative purposes only an example of an overview of facility equipment operating performance measurement of one embodiment. FIG. 1 shows a measuring and testing control server 100 is used to receive, process, and record measurements of operational performance levels of operating room 110 equipment. The measuring and testing control server 100 is also referred to herein as server 100 without any change in meaning. The operating room 110 equipment includes for example a humidifier 111, an air flow ventilator 112, an air conditioner 113, and lights 114.

The server is also used to receive, process, and record measurements of treatment room 120 equipment. The treatment room 120 equipment includes a humidifier 121, an air flow ventilator 122, and an air conditioner 123. The server is also used to receive, process, and record measurements of a procedure room 130, wherein the equipment includes a radiology x-ray machine 131, cardiology ECG devices 132, gynecological ultrasound 133 devices, and gynecology sonogram 134 devices.

Nursing rooms 140 have equipment including a crash cart defibrillator 141, medication refrigerator 142, autoclave sterilizers 143, patlent nourishment refrigerator 144, and patlent pulse and blood pressure detection device 145. The administrative offices 150 include at least one air conditioner 151.

DETAILED DESCRIPTION

Figure 2:
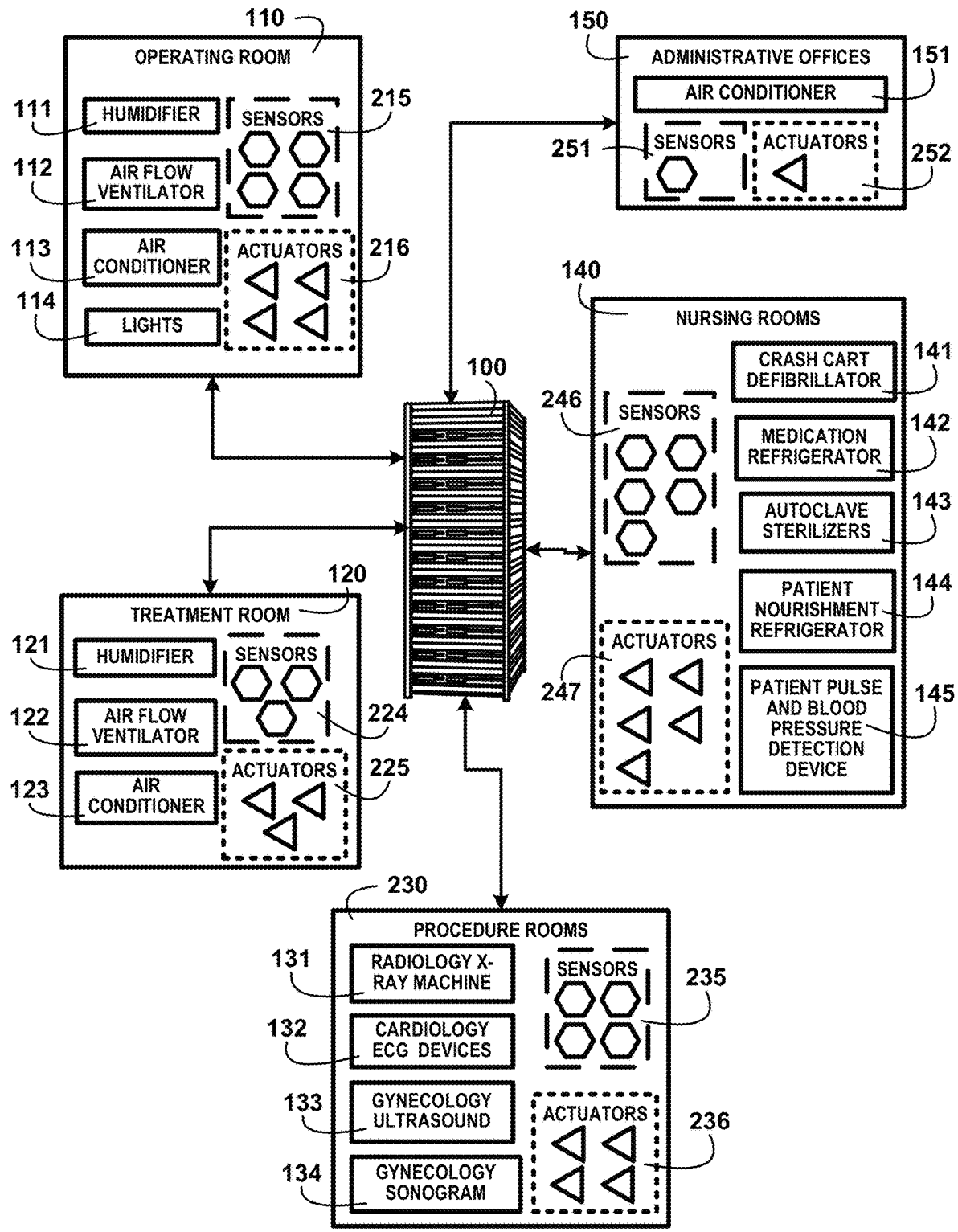
FIG. 2 shows for illustrative purposes only an example of facility equipment operating sensor measured performance and corrective actuators of one embodiment.

FIG. 2 shows for illustrative purposes only an example of facility equipment operating sensor measured performance and corrective actuators of one embodiment. FIG. 2 shows a server 100 used to receive wireless operating performance status of health care facility equipment, devices, and systems. The server 100 for example may receive a crash cart defibrillator battery charge sensor 246 signal that the crash cart defibrillator 141 is not charged sufficiently to produce the designed voltages. This is confirmed by a voltage sensor 246 that measures the voltage produced by the crash cart defibrillator 141. An operating room humidifier 111 humidity level is measured using a humidity sensor 215 that signals measurement of the humidity and transmits the measurement to the server 100.

An operating room air flow ventilator 112 air change frequency is measured using an air flow cfm sensor 215 that is used in the server 100 to calculate the changeover rate for the predetermined volume of air of the operating room. An operating room air conditioner 113 performance is measured using a temperature sensor 215 and transmitted wirelessly to the server 100. Operating room lights 114 luminescence level is measured using at least one lighting sensor 215. The at least one lighting sensor measurements are wirelessly transmitted to the server 100.

A medication refrigerator 142 temperature is measured using a temperature sensor 246 and the measurements are wirelessly transmitted to the server 100. Autoclave sterilizers 143 sterilize instruments at a predetermined temperature that is measured using a temperature sensor. The autoclave sterilizer's measured temperatures from the temperature sensor 246 are wirelessly transmitted to the server 100. A patient nourishment refrigerator 144 temperature is monitored with a temperature sensor 246 measuring the temperatures and transmitting wirelessly the temperature measurements to the server 100.

Each patient pulse and blood pressure detection device 145 is measured using a pressure sensor 246 to measure the accuracy of the patient pulse and blood pressure detection device 145. The pressure sensor 246 pressure measurements are wirelessly transmitted to the server 100. A gynecology sonogram 134 user graphic interface is measured using an image pixel sensor 235 and the image pixel sensor 235 measurements are wirelessly transmitted to the server 100. Gynecological ultrasound 133 devices are measured using a pressure sensor 235 to detect the strength of the ultrasound pressure imparted to the patient. The pressure sensor 235 measurements are wirelessly transmitted to the server 100. Cardiology ECG devices 132 are measured using an electronic signal sensor 235 to detect electronic signal strength from each of the ECG device leads that attach to the patient. The electronic signal sensor 235 measurements are wirelessly transmitted to the server 100.

A radiology x-ray machine 131 emits an x-ray beam at predetermined definitions. An x-ray beam defining detector 235 is used to measure the x-ray beam definitions and wirelessly transmit the measurements to the server 100. Patient admitting lobbies and rooms have frequent air changes to reduce the spread of infections. The patient admissions air flow ventilator operation is measured using an air flow cfm sensor and the measurement data is wirelessly transmitted to the server 100. Administration offices 150 air conditioner 151 is measured using a temperature sensor 251 and the measurements are wirelessly transmitted to the server 100.

Treatment room 120 air conditioner 123 operations are measured using a temperature sensor 224 whose measurements are wirelessly transmitted to the server 100. Treatment room 120 air flow ventilator 122 operations are monitored using measurements using an air flow cfm sensor 224. The air flow cfm sensor 224 measurements are wirelessly transmitted to the server 100. Treatment room 120 humidifier 121 devices are monitored for humidity levels using a humidity sensor 224 to measure the humidity level. The humidity level measurements of the humidity sensor 224 measurements are wirelessly transmitted to the server 100 of one embodiment.

FIG. 2 shows the server 100 wirelessly coupled to the operating room 110 including the equipment. The equipment in the operating room 110 includes the humidifier 111, air flow ventilator 112, air conditioner 113, and lights 114. The server 100 processes the sensor measurement to determine operational adjustment in the equipment. The server wirelessly transmits settings adjustment instruction to a settings actuator 225 coupled to each piece of equipment to make adjustments to the equipment operations. Settings actuators 216 are attached to each piece of operating room equipment to make the sensors 215 measurement adjustments transmitted by the server 100.

The server 100 wirelessly coupled to the treatment room 120 equipment including the humidifier 121, air flow ventilator 122, and air conditioner 123. Settings actuators 225 are attached to each piece of treatment room equipment 224 to make the sensors 2224 measurement adjustments transmitted by the server 100.

The server 100 wirelessly coupled to the procedure room 130 equipment including the radiology x-ray machine 131, cardiology ECG devices 132, gynecological ultrasound 133, and gynecology sonogram 134. Settings actuators 236 are attached to each piece of procedure room equipment to make the sensors 235 measurement adjustments transmitted by the server 100.

The server 100 wirelessly coupled to the nursing rooms 140 equipment including the crash cart defibrillator 141, medication refrigerator 142, autoclave sterilizers 143, patient nourishment refrigerator 144, and patient pulse and blood pressure detection device 145. Settings actuators 247 are attached to each piece of nursing room equipment to respond to sensors 246 measurement settings adjustments wirelessly transmitted the server 100.

The server 100 wirelessly coupled to the administrative offices 150 air conditioner 151. Settings actuators 252 are attached to each piece of administrative offices equipment. The server 100 having received the measurement data from the sensors 251 processes the data to determine any equipment performance adjustments which should be made. The server 100 includes instructions recorded in a database to activate actuators 252 to adjust equipment settings. The server 100 wirelessly transmits settings adjustments to actuators 252 coupled to the equipment to correct any performance measurements that do not meet predetermined ranges of performance measurements meeting compliance standards. In one example the crash cart defibrillator 141 may receive charger settings actuators 247 instructions to increase charging settings to recharge the defibrillator to a full charge in less time. A voltage regulator adjustment for the crash cart defibrillator to maintain voltage output within predetermined voltages meeting compliance standards.

The humidity level measurements are used to determine any operating room 110 humidifier 111 settings actuators 216 adjustments to meet the predetermined ranges of humidity levels. The settings actuators adjustments are transmitted wirelessly for each piece of equipment to facilitate the changes in the settings. The operating room 110 air flow ventilator 112 air volume changeover measurements are used to determine the changes wirelessly transmitted to an air flow settings actuator 216. The operating room 110 air conditioner 113 temperature measurements are used to determine the changes wirelessly transmitted to a thermostat settings actuators 216. The operating room 110 lights lighting level measurements are used to determine the changes wirelessly transmitted to a lighting settings actuators 216.

The medication refrigerator 142 temperature measurements are used to determine the changes wirelessly transmitted to a thermostat settings actuators 247. The autoclave sterilizers 143 temperature measurements are used to determine the changes wirelessly transmitted to a thermostat settings actuators 247. The patient nourishment refrigerator 144 temperature measurements are used to determine the changes wirelessly transmitted to a thermostat settings actuators 247.

The patient pulse and blood pressure detection device 145 pressure measurements are used to determine the changes wirelessly transmitted to a calibration settings actuators 247. The gynecology sonogram 134 user graphic interface pixel sensor measurements are used to determine the changes wirelessly transmitted to a resize pixel actuators 236. The gynecological ultrasound 133 devices pressure measurements are used to determine the changes wirelessly transmitted to a calibration settings actuators 236.

The cardiology ECG devices 132 electrical signal strength measurements are used to determine the changes wirelessly transmitted to an electronic calibration settings actuators 236. The radiology x-ray machine 131 x-ray beam measurements are used to determine the changes wirelessly transmitted to an x-ray beam settings actuators 236. The administration offices 150 air conditioner 151 temperature measurements are used to determine the changes wirelessly transmitted to a thermostat settings actuators 252.

The treatment room 120 air conditioner 123 temperature measurements are used to determine the changes wirelessly transmitted to a thermostat settings actuators 225. The treatment room 120 air flow ventilator 122 air volume changeover measurements are used to determine the changes wirelessly transmitted to an air flow settings actuators 225. The treatment room 120 humidifier 121 humidity level measurements are used to determine the changes wirelessly transmitted to a humidifier settings actuators 225 of one embodiment.

Figure 3:
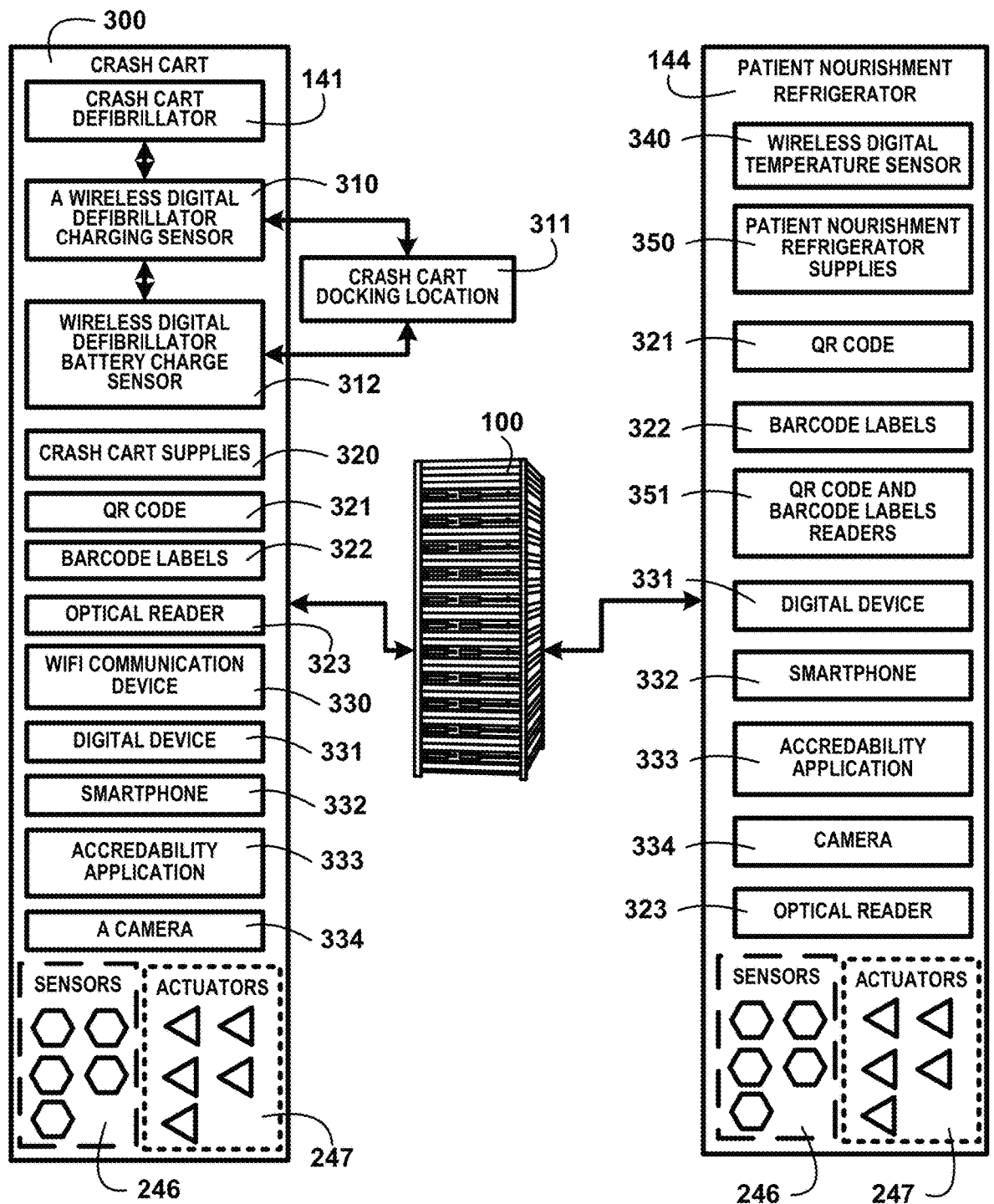
FIG. 3 shows for illustrative purposes only an example of a flow chart of an ambulatory health care company accreditation equipment compliance method and devices of one embodiment.

An Ambulatory Health Care Company Accreditation Equipment Compliance:

FIG. 3 shows for illustrative purposes only an example of a flow chart of an ambulatory health care company accreditation equipment compliance of one embodiment. FIG. 3 shows a crash cart 300 including a crash cart defibrillator 141. A wireless digital defibrillator charging sensor 310 is coupled between the crash cart defibrillator 141 and a crash cart docking location 311. The wireless digital defibrillator charging sensor 310 is used to measure the charging rate of the defibrillator from a power source located at the crash cart docking location 311. A wireless digital defibrillator battery charge sensor 312 coupled to the crash cart defibrillator 141 is used to measure the charge on the crash cart defibrillator 141 to determine it's readiness for use.

Actuators 247 coupled to the wireless digital defibrillator charging sensor 310 and wireless digital defibrillator battery charge sensor 312 are used to adjust the settings on the wireless digital defibrillator charging sensor 310 and wireless digital defibrillator battery charge sensor 312 to regulate the charging rate and battery charge of the crash cart defibrillator 141 based on instructions transmitted to the actuators 247 from the server 100.

Crash cart supplies 320 are marked using at least one QR code 321 and at least one of unique barcode labels 322. A camera 334 of a digital device 331 including a user's smartphone 332 is used to capture an image of crash cart supplies 320 at least one QR code 321 and at least one of unique barcode labels 322. An optical reader 323 is used to identify and measure the number of crash cart supplies 320 based on the at least one QR code 321 and at least one of unique barcode labels 322.

The optical reader 323 identification and number of associated crash cart supplies 320 is transmitted using a WIFI communication device 330 to the server 100. The server 100 processes the data to create an inventory of the crash cart supplies 320 to determine if it is within a predetermined range based on the compliance standards. The server 100 produced inventory is transmitted to a accredability application 333 installed on the user's smartphone 332 to inform the user of any deficiencies in the crash cart supplies 320 the user will need to replenish to meet the predetermined range based on the compliance standards.

The patient nourishment refrigerator 144 includes at least one wireless digital temperature sensor 340. The at least one wireless digital temperature sensor 340 measures the temperature of the patient nourishment refrigerator 144. Actuators 247 coupled to the patient nourishment refrigerator 144 are transmitted settings adjustments from the server 100 to adjust the temperature settings to be within the predetermined range within the compliance standards.

Patient nourishment refrigerator supplies 350 are marked with a QR code 321 and barcode labels 322. A user's digital device 331 including a smartphone 332 having an accredability application 333 is used to capture an image of the Patient nourishment refrigerator supplies 350 using for example a camera 334 of the smartphone 332. The accredability application 333 transmits the captured patient nourishment refrigerator supplies 350 to the server 100 optical reader 323. The optical reader 323 includes QR code and barcode labels readers 351 used to identify and measure the numbers of the patient nourishment refrigerator supplies 350.

The optical reader 323 identifications and measurements of patient nourishment refrigerator supplies 350 are transmitted to the server 100. The server 100 processes the information transmitted to generate an inventory of the patient nourishment refrigerator supplies 350. The inventory is transmitted to the user's smartphone 332 to alert the user of any shortages of patient nourishment refrigerator supplies 350 to replenish those supplies to meet predetermined amounts to be within ranges of compliance standards of one embodiment.

Figure 4:
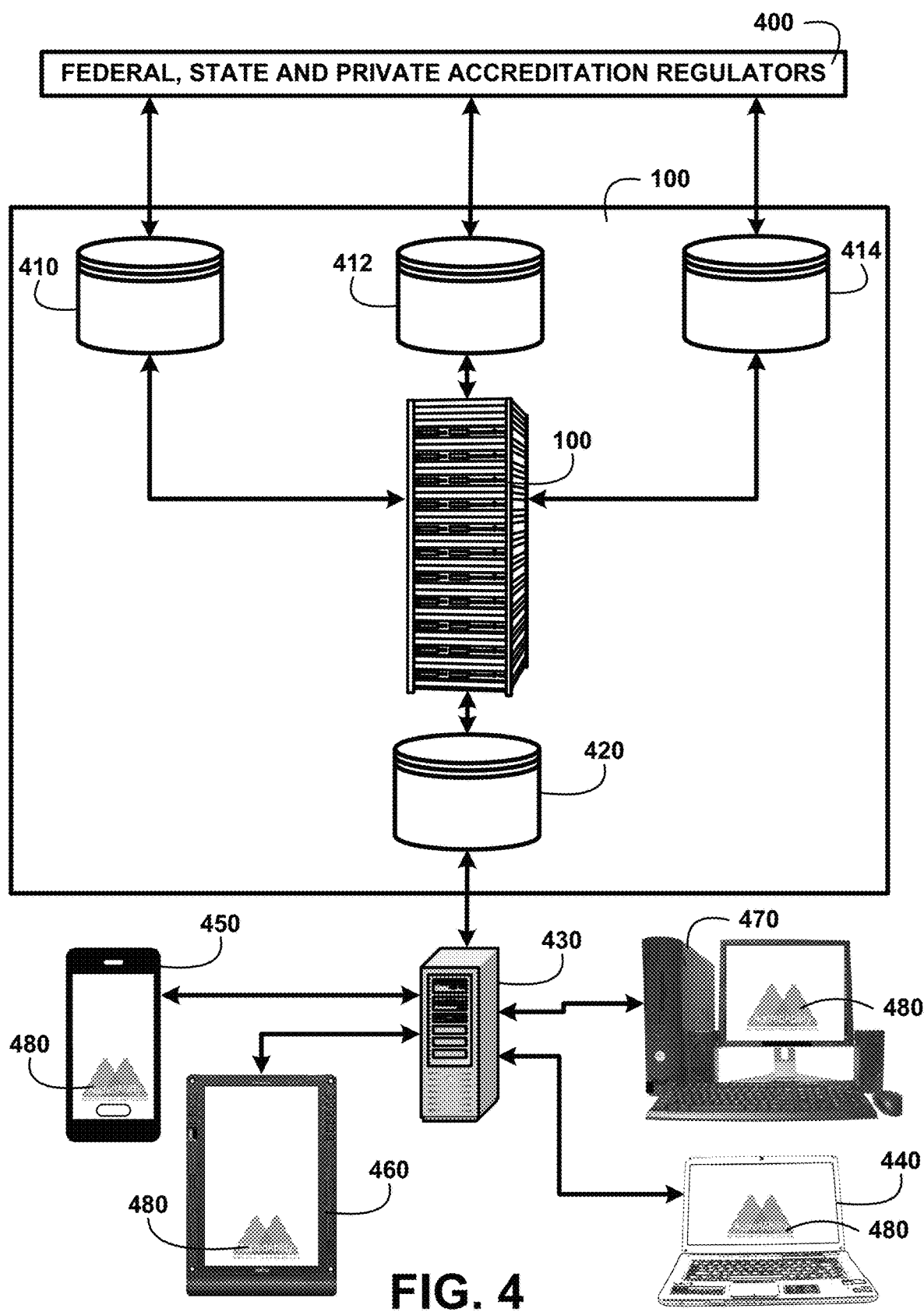
FIG. 4 shows for illustrative purposes only an example of an automatic accreditation standards and regulations updating process of one embodiment.

An Automatic Accreditation Standards and Regulations Updating Process:

FIG. 4 shows for illustrative purposes only an example of an automatic accreditation standards and regulations updating process of one embodiment. FIG. 4 shows the AccredAbility server 100 downloading from federal, state and private accreditation regulators 400 changes, modifications and new issues to update a federal accreditation database 410, a state accreditation database 412, and private accreditation database 414. The AccredAbility server 100 populates at least one updated accreditation standards and regulations database 420 with specific accreditation standards and regulations applicable to a registered company profile. The populated specific accreditation standards and regulations are downloaded to a registered company server 430. The registered company staff can remotely access functions of the registered company server 430 using the AccredAbility application 480 installed on a digital device including a smart phone 450, a tablet 460, a computer 470 and a laptop computer 440 of one embodiment.

Figure 5:
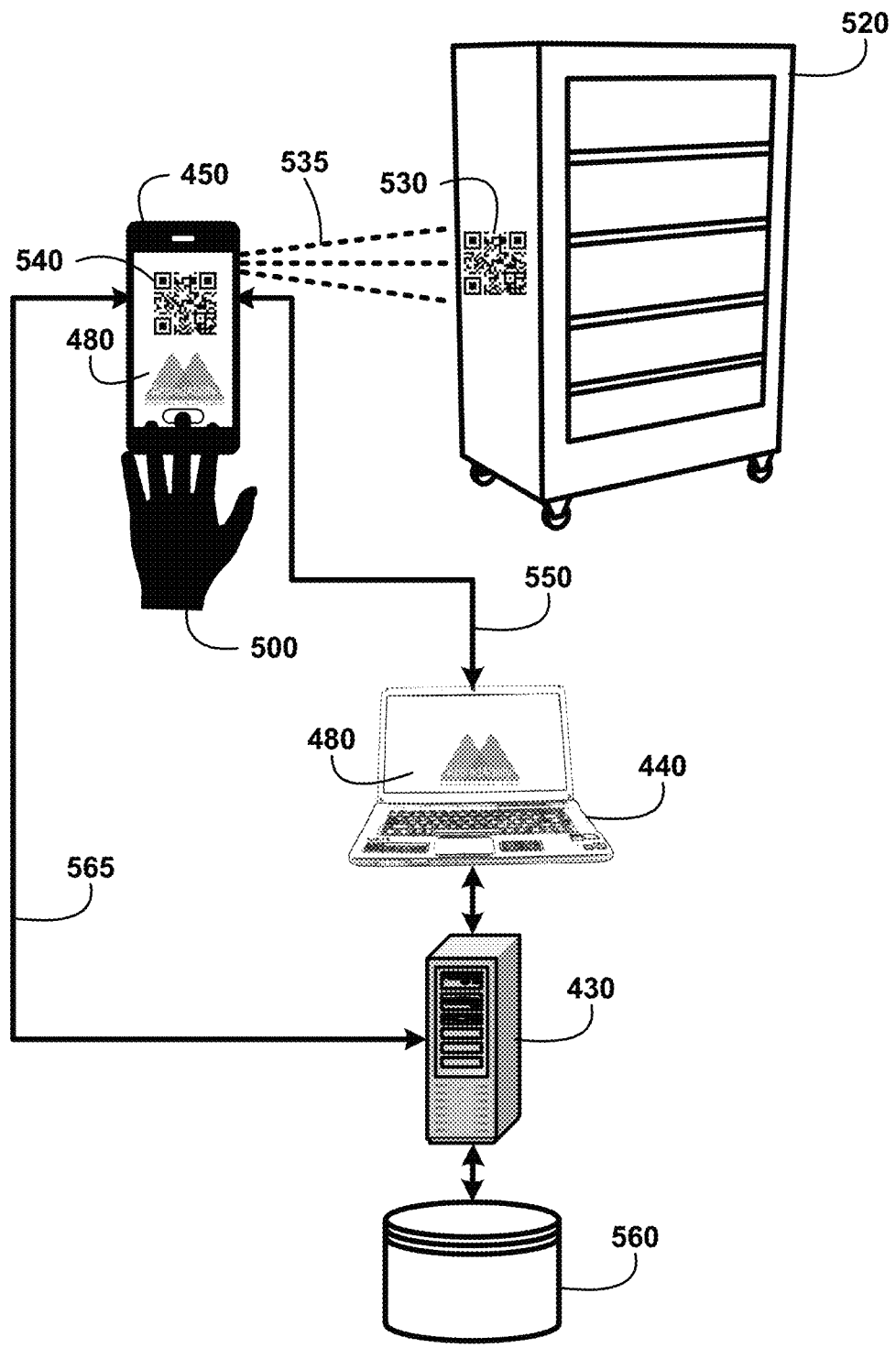
FIG. 5 shows for illustrative purposes only an example of an equipment compliance process of one embodiment.

An Equipment Compliance Process:

FIG. 5 shows for illustrative purposes only an example of an equipment compliance process of one embodiment. FIG. 5 shows a user 500 activating a camera of the smart phone 450 with the AccredAbility application 480. The user 500 is using the smart phone camera to take a photo of a QR code 535 coupled to a registered company piece of equipment 520 for example a medication refrigerator. The registered company piece of equipment 520 is identified with a coupled QR code 530. Upon capturing a QR code image 540, the QR code image 540 is transmitted over WIFI to a laptop computer 550. The laptop computer 440 with the AccredAbility application 480 is used to transmit the QR code image to the registered company server 430 as part of an equipment compliance process and recorded in a registered company equipment database 560. The QR code image 540 may be transmitted to the registered company server directly 565. In a compliance process the registered company server 430 records the QR code image 540 and coded data on the registered company equipment database 560 as part of an equipment compliance process including an equipment inventory of one embodiment.

Figure 6:
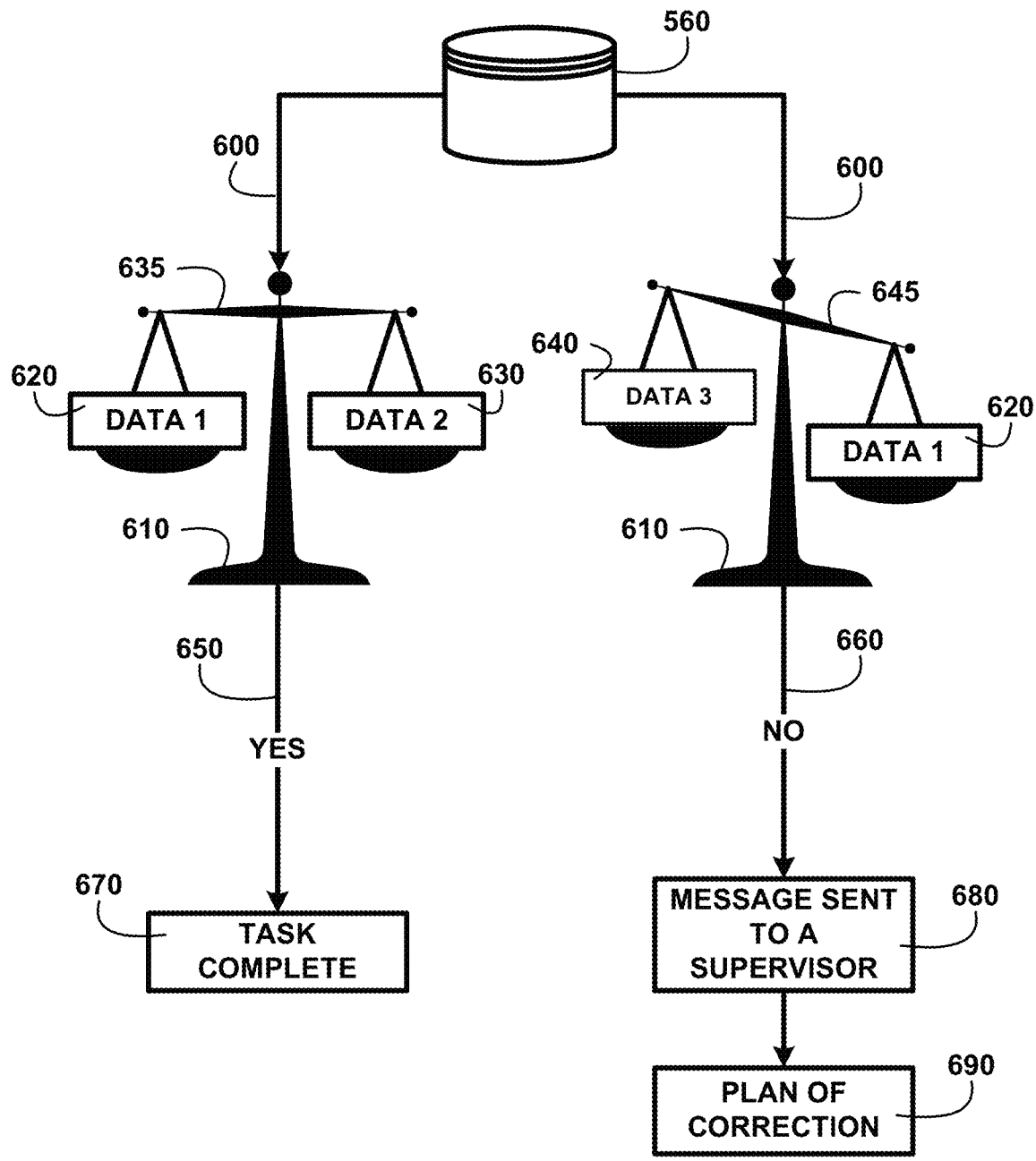
FIG. 6 shows for illustrative purposes only an example of a process for determining compliance of one embodiment.

A Process of Determining Compliance:

FIG. 6 shows for illustrative purposes only an example of a process for determining compliance of one embodiment. FIG. 6 shows the registered company equipment database 560 using for example a QR code identified piece of equipment operational log of recorded accreditation compliance data 600 for performing an analytical evaluation process 610 on the AccredAbility server 100 of FIG. 1. A scale is shown as an illustrative representation only of the analytical evaluation process 610 for determining an accreditation compliance status of the QR code identified piece of equipment. Data 1 620 is the accreditation compliance from the updated standards and regulations applicable for the QR code identified piece of equipment. Data 2 630 for example is one set of recorded accreditation compliance data for an operational period of time for the QR code identified piece of equipment. Data 2 is evaluated against data 1 635. The data 2 630 analytical determination results in a positive finding of yes 650 for that period of time the identified piece of equipment is accreditation compliant 650. The accreditation compliant result is recorded and a compliance task complete indication is recorded 670.

Data 3 640 is another set of recorded accreditation compliance data for an operational period of time for the QR code identified piece of equipment. Data 3 is evaluated against data 1 645. The data 3 640 analytical determination results in a negative finding of no 660 for that period of time the identified piece of equipment is accreditation non-compliant 660. The negative finding triggers an alert message sent to a supervisor 680 wherein the supervisor determines a plan of correction 690 of one embodiment.

Figure 7:
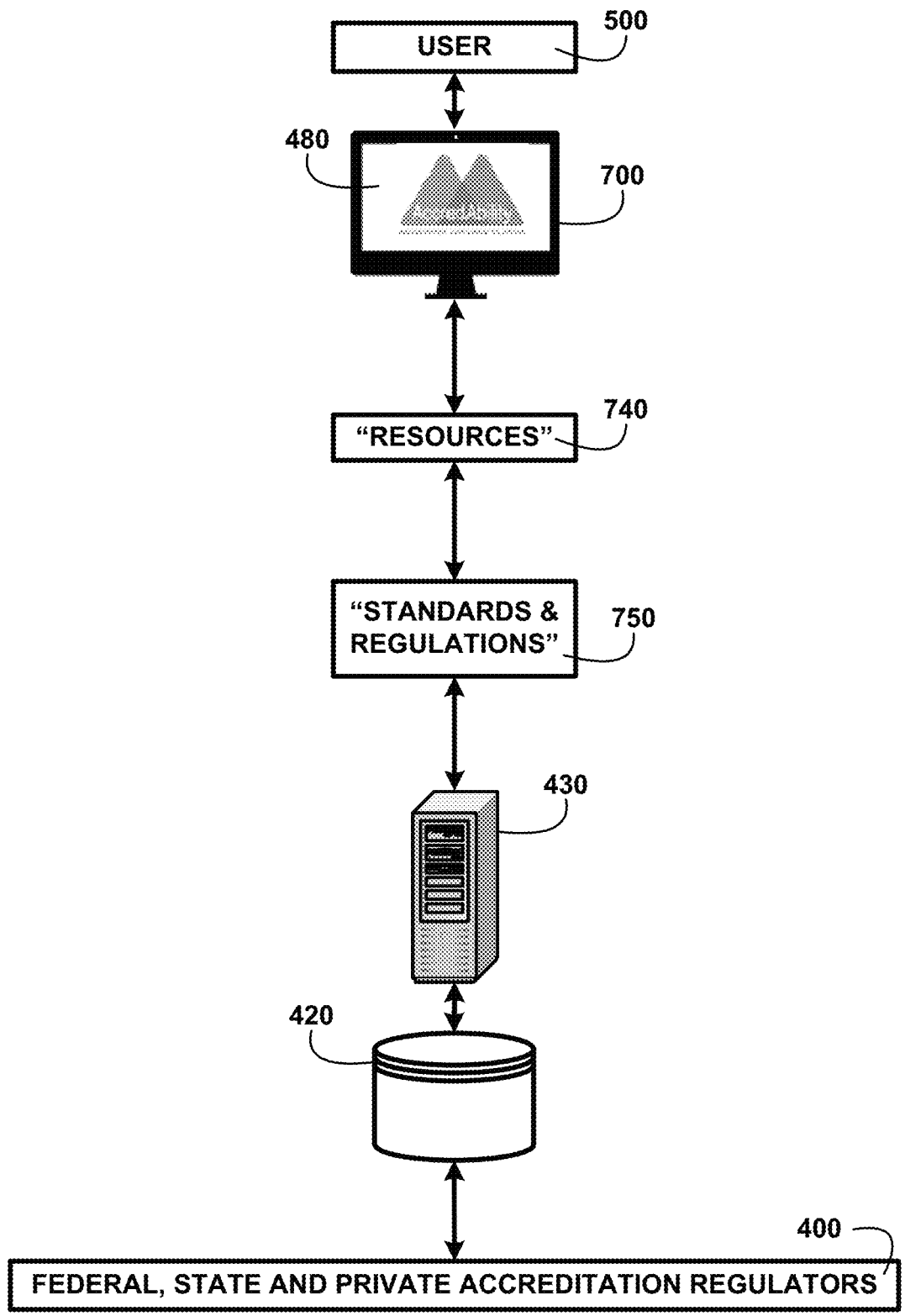
FIG. 7 shows for illustrative purposes only an example of accessing updated standards and regulations of one embodiment.

Accessing Updated Standards and Regulations:

FIG. 7 shows for illustrative purposes only an example of accessing updated standards and regulations of one embodiment. FIG. 7 shows the user 500 for example a member of a company governing board using a digital device for example a computer 700 and the AccredAbility application 480 for accessing updated standards and regulations. The user can click on a "resources" 740 tab on the main menu then click on a "standards and regulations" 750 tab. The AccredAbility application website platform will then connect to the registered company server 430. The registered company server 430 will direct the user to their company updated standards and regulations database 420. The updated standards and regulations database 420 will display on the computer screen federal, state and private accreditation regulators 400 updated standards and regulations. This process allows users to access accreditation compliance guidelines all in one place with ease.

Figure 8A:
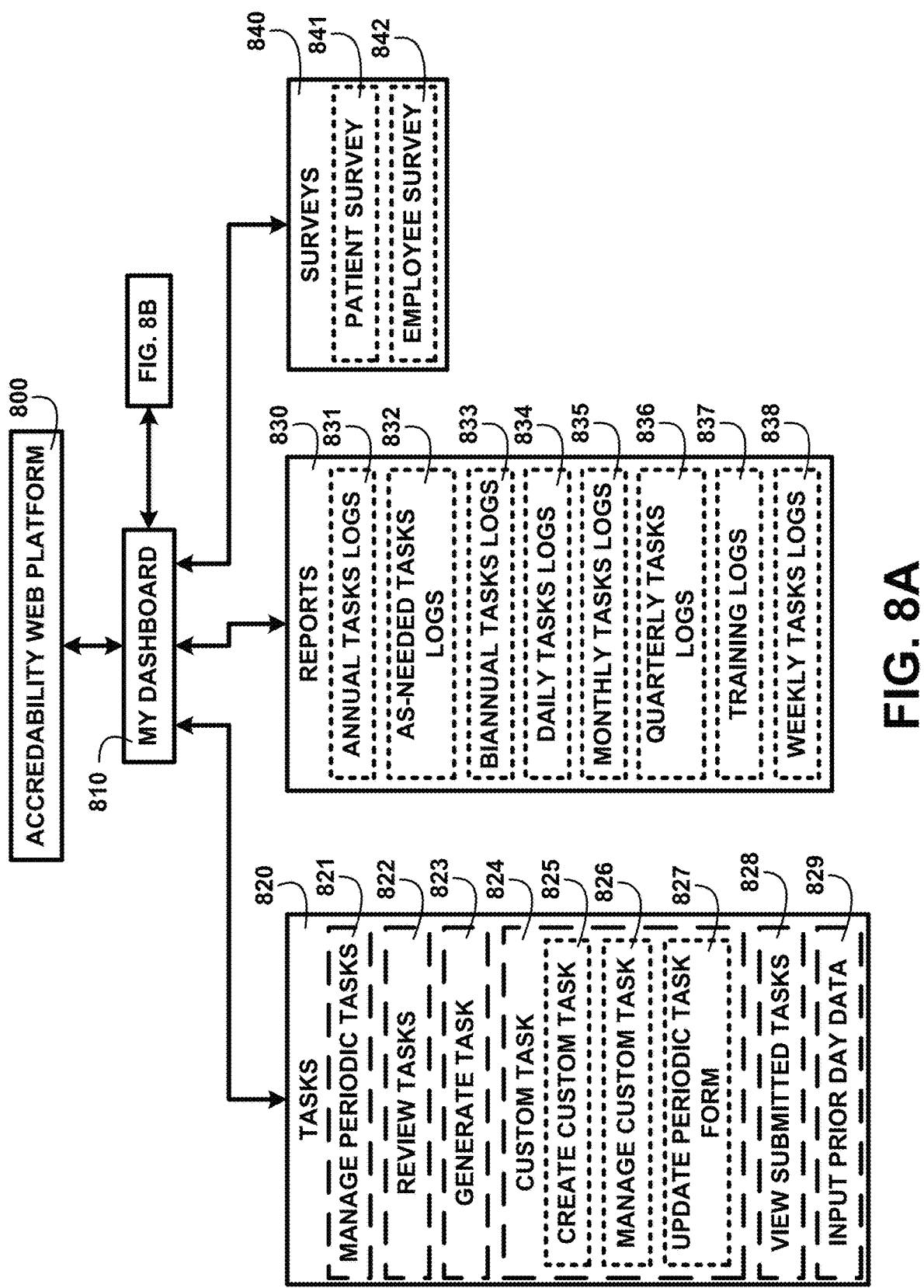
FIG. 8A shows for illustrative purposes only an example of displaying a web platform dashboard of one embodiment.

Displaying a Web Platform Dashboard:

FIG. 8A shows for illustrative purposes only an example of displaying a web platform dashboard of one embodiment. FIG. 8A shows an AccredAbility web platform 800 displaying on a computer screen, not shown, a my dashboard 810 web page. The my dashboard 810 shows a user selection of tabs that can be clicked by the user to select an area of interest. In this example one area of interest may be tasks 820. Upon clicking the tasks 820 tab multiple selections are displayed from which the user can make a subsequent selection. Tasks 820 subsequent selections include for example manage periodic tasks 821, review tasks 822, generate task 823, custom task 824, create custom task 825, manage custom task 826, update periodic task form 827, view submitted tasks 828, and input prior day data 829.

Another tab is reports 830 which includes for example annual tasks logs 831, as-needed tasks logs 832, biannual tasks logs 833, daily tasks logs 834, monthly tasks logs 835, quarterly tasks logs 836, training logs 837, and weekly tasks logs 838.

A third tab is for selecting surveys 840. Surveys 840 include for example patient survey 841 and employee survey 842. The my dashboard 810 web page is further described in FIG. 8B.

Figure 8B:
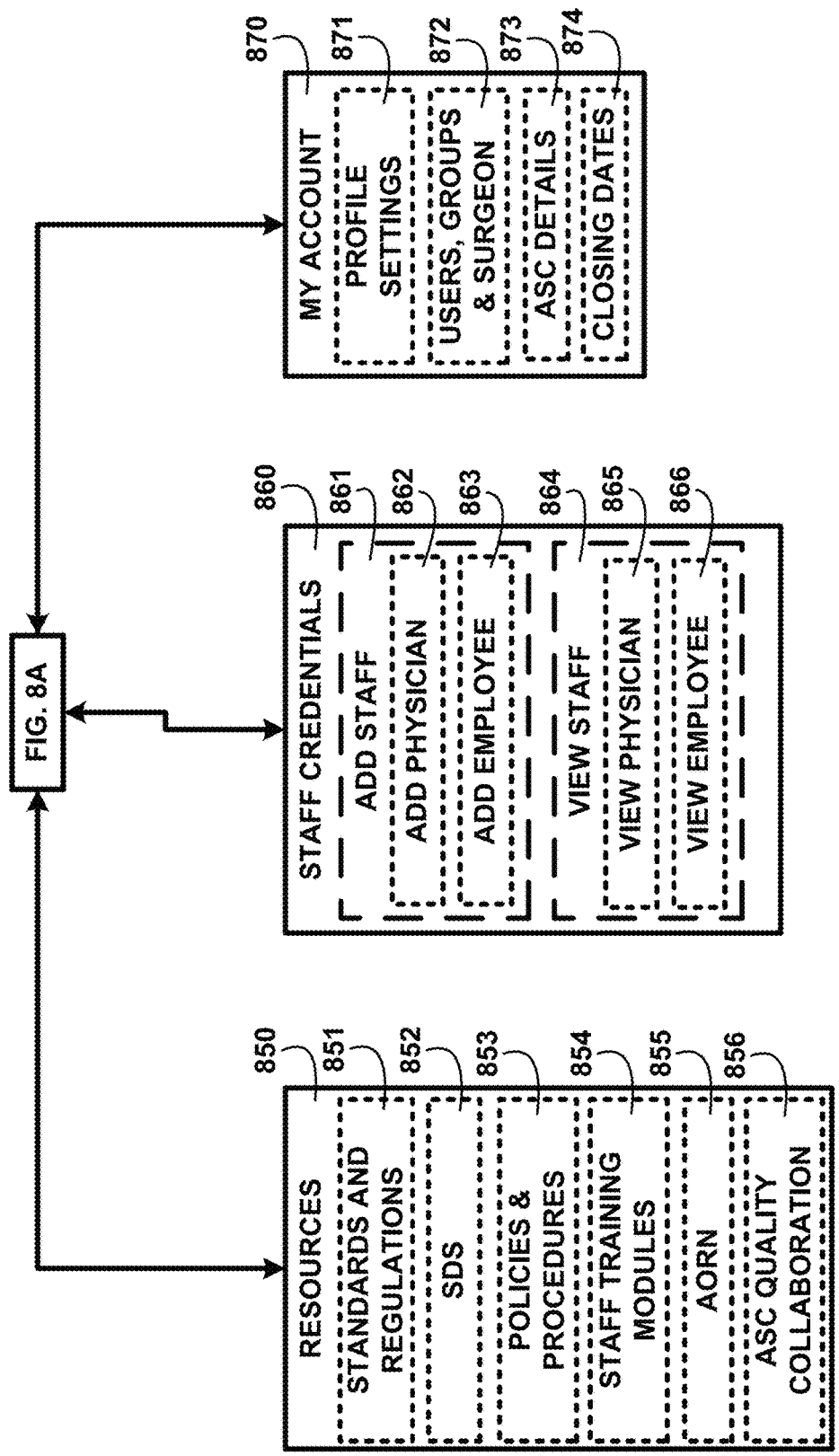
FIG. 8B shows for illustrative purposes only an example of a continuation of displaying a web platform dashboard of one embodiment.

A Continuation of Displaying a Web Platform Dashboard:

FIG. 8B shows for illustrative purposes only an example of a continuation of displaying a web platform dashboard of one embodiment. FIG. 8B shows continuing from FIG. 8A additional my dashboard 810 of FIG. 8A web page selections including resources 850 that includes standards and regulations 851, SDS 852, policies & procedures 853, staff training modules 854, aorn 855, and ASC quality collaboration 856. Another tab is staff credentials 860 including add staff 861, to further select add physician 862 and add employee 863. A view staff 864 tab includes view physician 865 and view employee 866 selections.

A final my dashboard 810 of FIG. 8A web page selection in this example is my account 870. My account 870 when clicked provides selections including profile settings 871, users, groups & surgeon 872, ASC details 873, and closing dates 874 of one embodiment.

Figure 9:
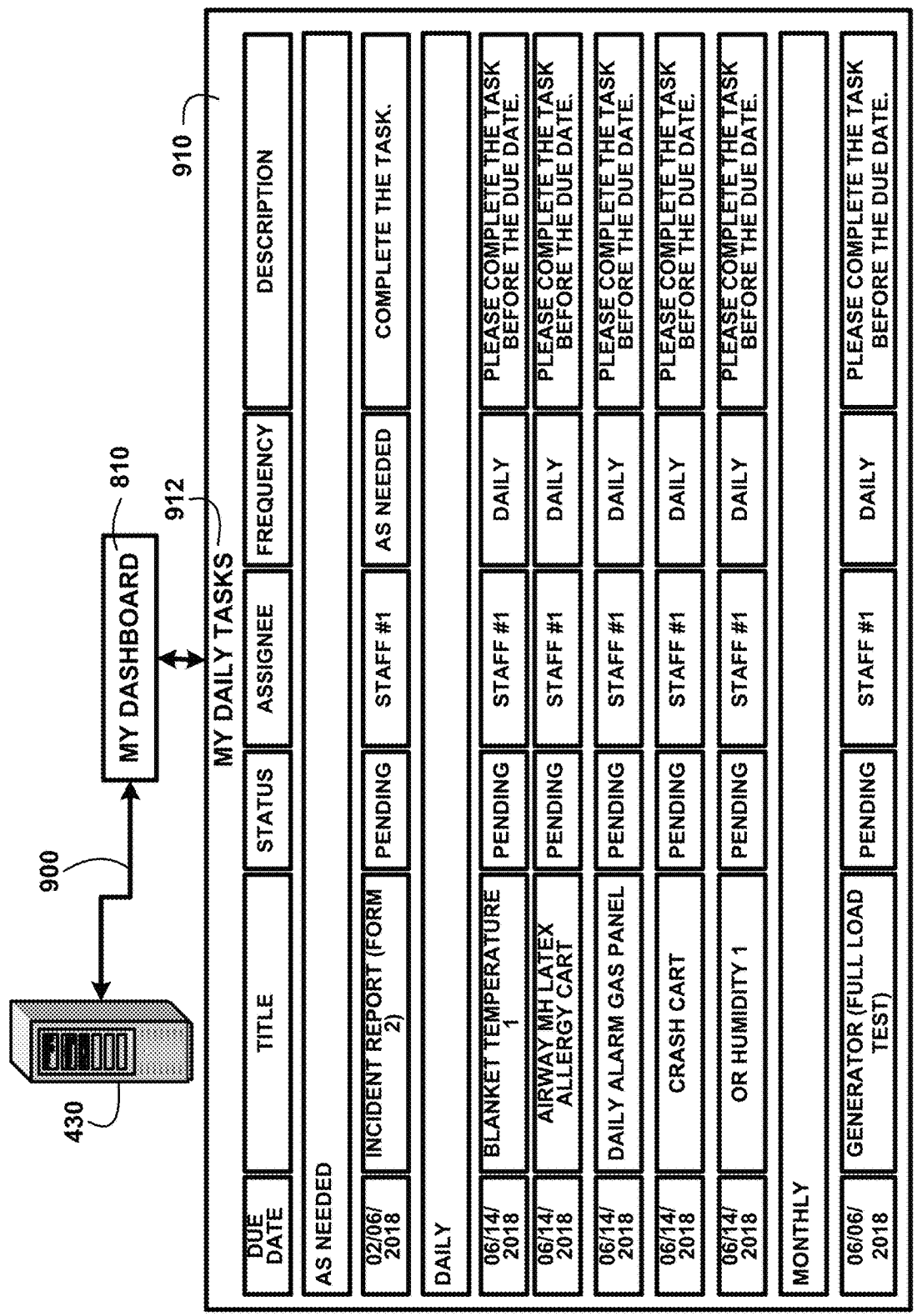
FIG. 9 shows for illustrative purposes only an example of displaying user tasks of one embodiment.

Displaying User Tasks:

FIG. 9 shows for illustrative purposes only an example of displaying user tasks of one embodiment. FIG. 9 shows the registered company server 430 displaying on a computer screen 900, not shown, the my dashboard 810 web page with a my tasks 910 listing for a user daily tasks 912. The users' daily tasks 912 include a due date, title, status, assignee, frequency, and description. The user can setup the AccredAbility application 480 of FIG. 4 to automatically open and display daily the my dashboard 810 web page with a my tasks 910 listing for user daily tasks 912 when the user starts their digital device of one embodiment.

Figure 10:
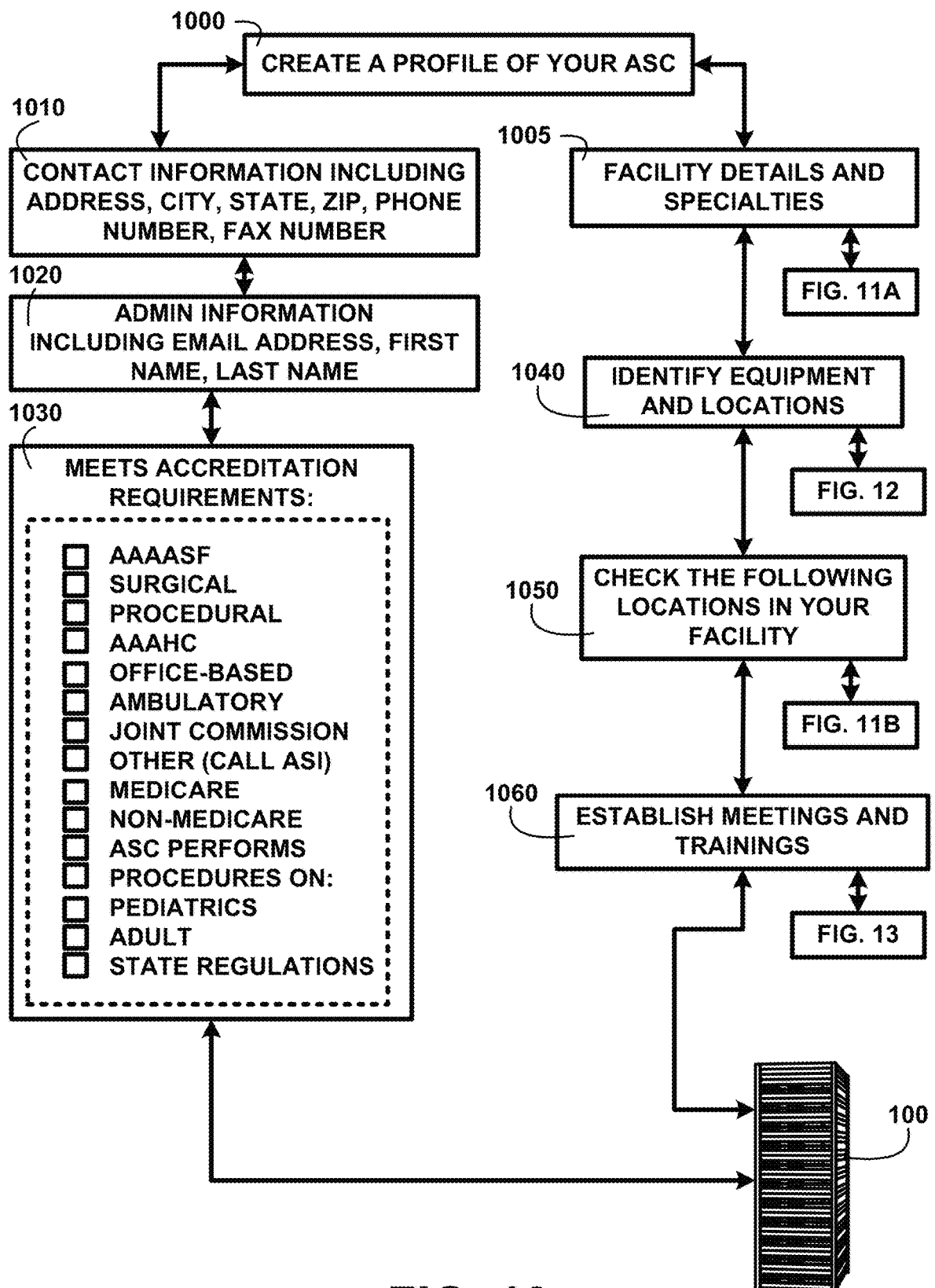
FIG. 10 shows for illustrative purposes only an example of creating a user profile of one embodiment.

Creating a User Profile:

FIG. 10 shows for illustrative purposes only an example of creating a user profile of one embodiment. FIG. 10 shows an AccredAbility application 480 of FIG. 4 web page on a computer screen not shown to create a profile of your ASC 1000. The profile will include for example contact information including address, city, state, zip, and phone number, and fax number 1010, admin information including email address, first name, and last name 1020. The profile also include a check list for the company which meets accreditation requirements: 1030 wherein a user checks a box next to all applicable accreditation agencies and types associated with their company. The information is uploaded and recorded on the AccredAbility server 100. A user continues to input company information including facility details and specialties 1005 on FIG. 11*a*, identify equipment and locations 1040 on FIG. 12, check the following locations in your facility 1050 on FIG. 11*b* and establish meetings and trainings 1060 on FIG. 13 of one embodiment.

Figure 11A:
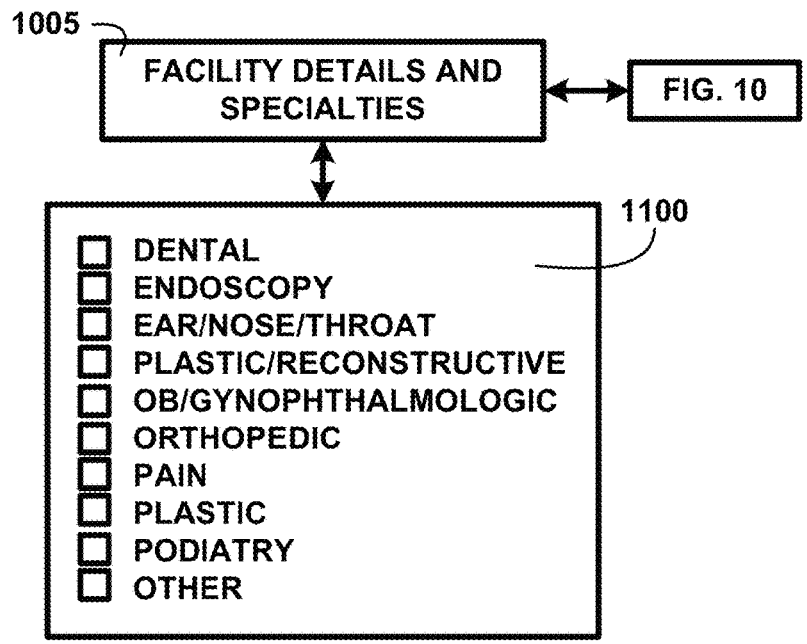
FIG. 11A shows for illustrative purposes only an example of a user input of facility details specialties of one embodiment.

A User Input of Facility Details Specialties:

FIG. 11A shows for illustrative purposes only an example of a user input of facility details specialties of one embodiment. FIG. 11A shows a continuation from FIG. 10 where the user continues inputting company information including facility details and specialties 1005 including medical and health care specialties wherein the user checks the box next to an applicable specialty 1100. The applicable specialty 1100 includes for example plastic/reconstructive. The checked boxes information is uploaded and recorded on the AccredAbility server 100 of FIG. 1 as shown in FIG. 10 of one embodiment.

Figure 11B:
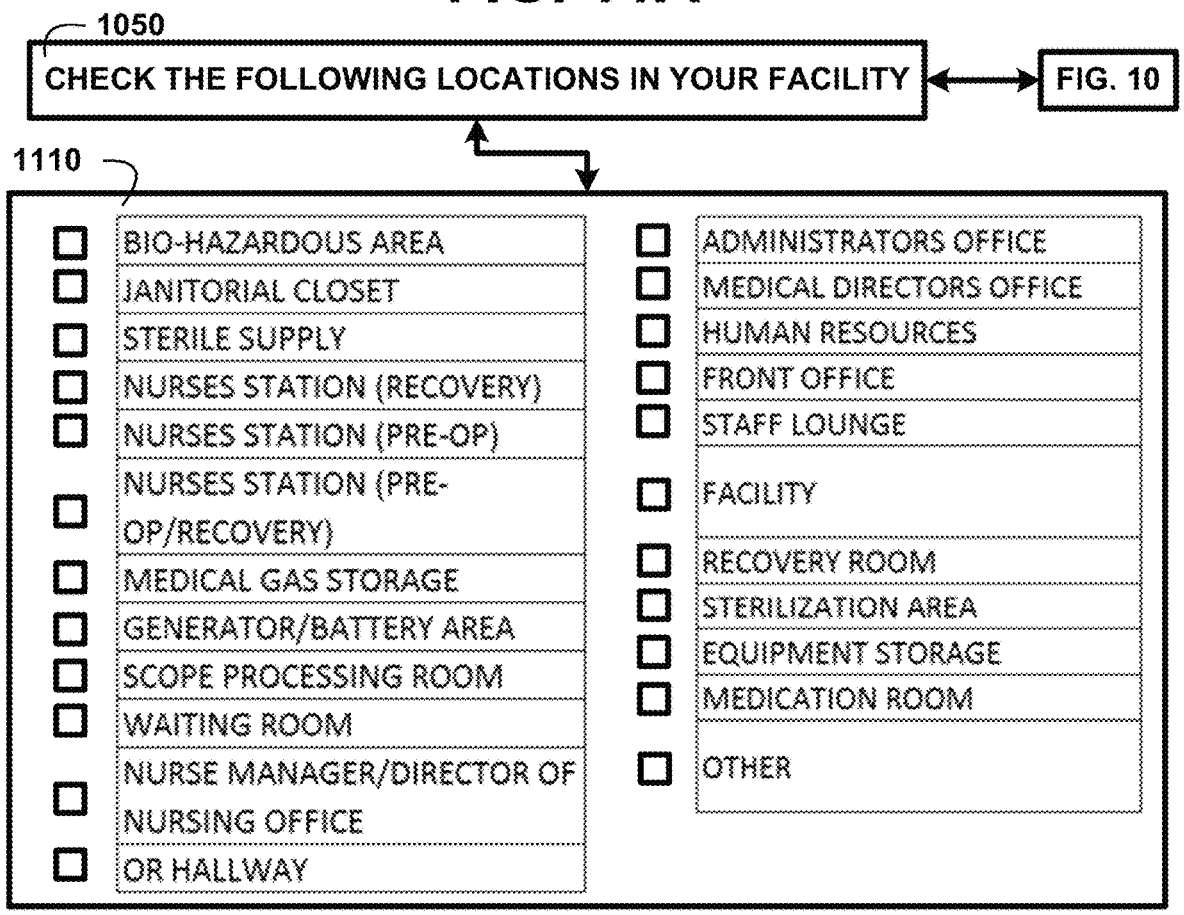
FIG. 11B shows for illustrative purposes only an example of a user input of locations in a facility of one embodiment.

A User Input of Locations in a Facility:

FIG. 11B shows for illustrative purposes only an example of a user input of locations in a facility of one embodiment. FIG. 11B shows from FIG. 10 the user continuing inputting company information including check the following locations in your facility 1050. The user checks the box next to applicable types of location descriptions 1110 for example nurses station (pre-op). The checked boxes information is uploaded and recorded on the AccredAbility server 100 of FIG. 1 as shown in FIG. 10 of one embodiment.

Figure 12:
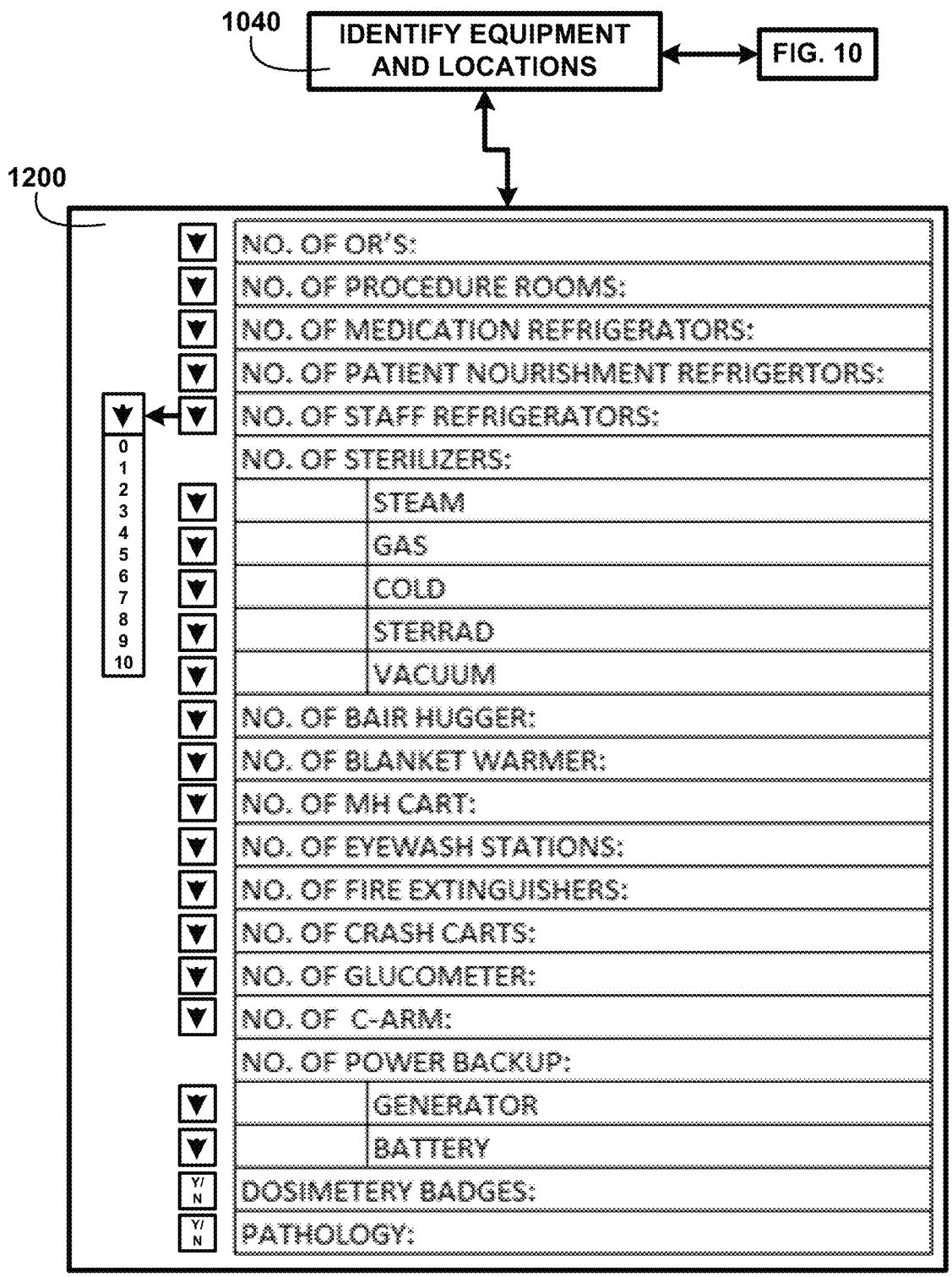
FIG. 12 shows for illustrative purposes only an example of a user input to identify equipment and locations of one embodiment.

A User Input to Identify Equipment and Locations:

FIG. 12 shows for illustrative purposes only an example of a user input to identify equipment and locations of one embodiment. FIG. 12 shows a continuation from FIG. 10 where the user continues inputting company information including identify equipment and locations 1040. The user clicks on a drop down icon and selects the number of the particular equipment description to show how many pieces of that equipment are located in the facility 1200. A particular equipment description includes for example a no. of staff refrigerators. Some types of equipment have a drop down icon that displays when clicked a yes or no (y/n) selection to indicate whether for example the facility includes a pathology lab. The checked boxes information is uploaded and recorded on the AccredAbility server 100 of FIG. 1 as shown in FIG. 10 of one embodiment.

Figure 13:
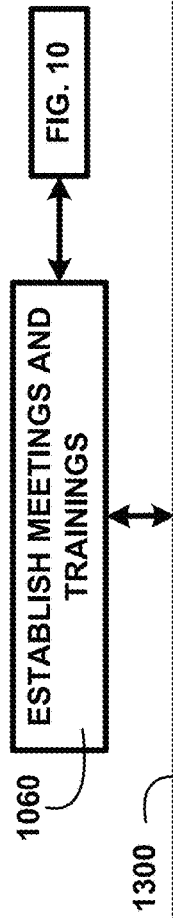
FIG. 13 shows for illustrative purposes only an example of a user input to establish meetings and trainings of one embodiment.

A User Input to Establish Meetings and Trainings:

FIG. 13 shows for illustrative purposes only an example of a user input to establish meetings and trainings of one embodiment. FIG. 13 shows a user continuing to input company information from FIG. 10. The additional company information includes information to establish meetings and trainings 1060. A check list 1300 of types of meetings and trainings are displayed on a user computer screen 1 not shown. The user checks a box next to a selected meeting description then using a drop down selector selects for example a month or meeting schedule frequency for the checked selected meeting. Some meetings only offer a yes or no (y-n) selection to indicate that type of described meeting is held or not. The checked boxes information is uploaded and recorded on the AccredAbility server 100 of FIG. 1 as shown in FIG. 10 of one embodiment.

Figure 14:
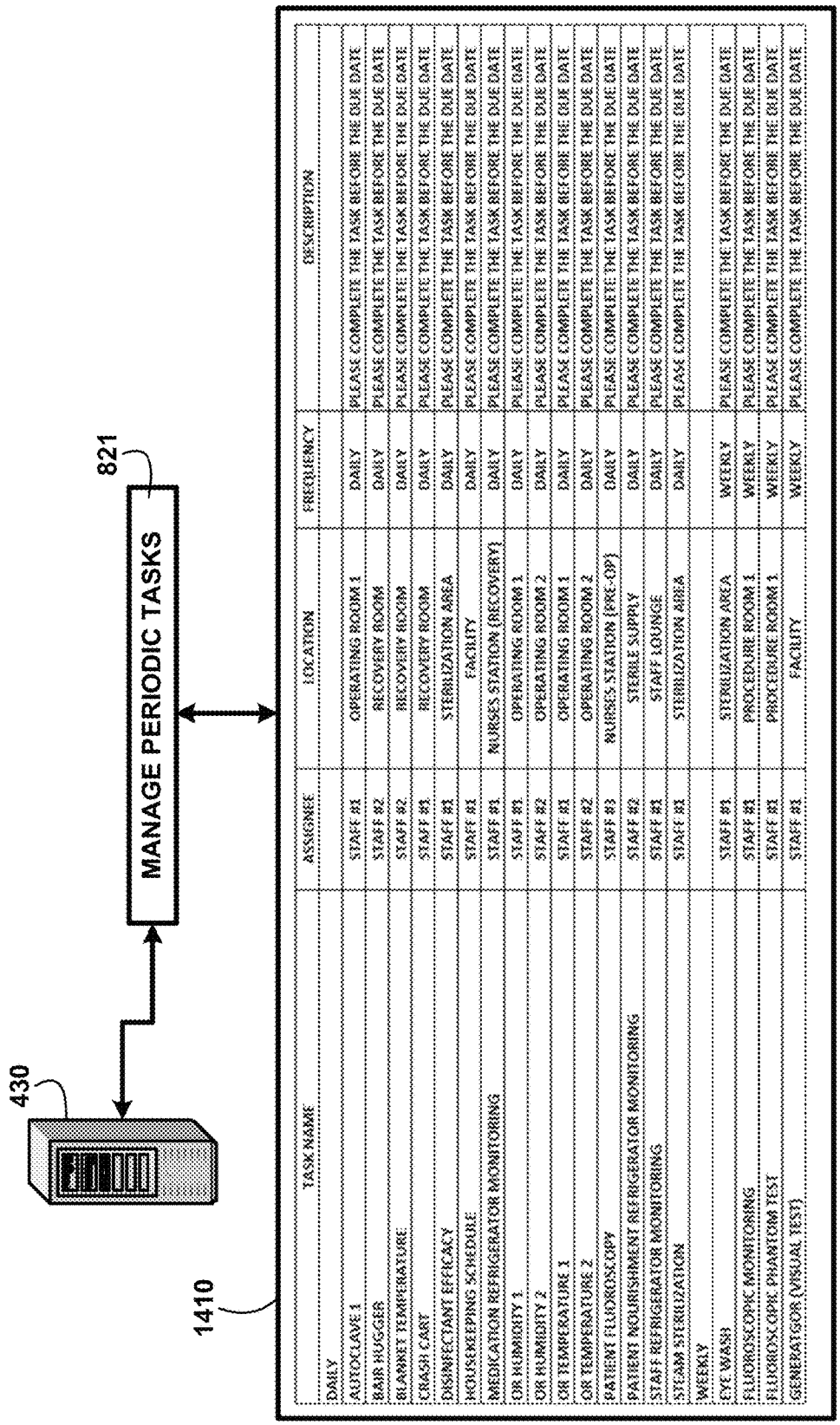
FIG. 14 shows for illustrative purposes only an example of a display to manage periodic tasks of one embodiment.

A Display to Manage Periodic Tasks:

FIG. 14 shows for illustrative purposes only an example of a display to manage periodic tasks of one embodiment. FIG. 14 shows the registered company server 430 displaying on a computer screen not shown a manage periodic tasks 821 listing of tasks and assignees 1410. The listing includes a task name, the name of a task assignee, a location of the task, the frequency of the task and a description of the task. An example shown is a crash cart task assigned to staff #1. The crash cart is located in a recovery room and the task is to be completed daily. The manage periodic tasks 821 is used by a supervisor to review an assignee performance of task completions of one embodiment.

Figure 15:
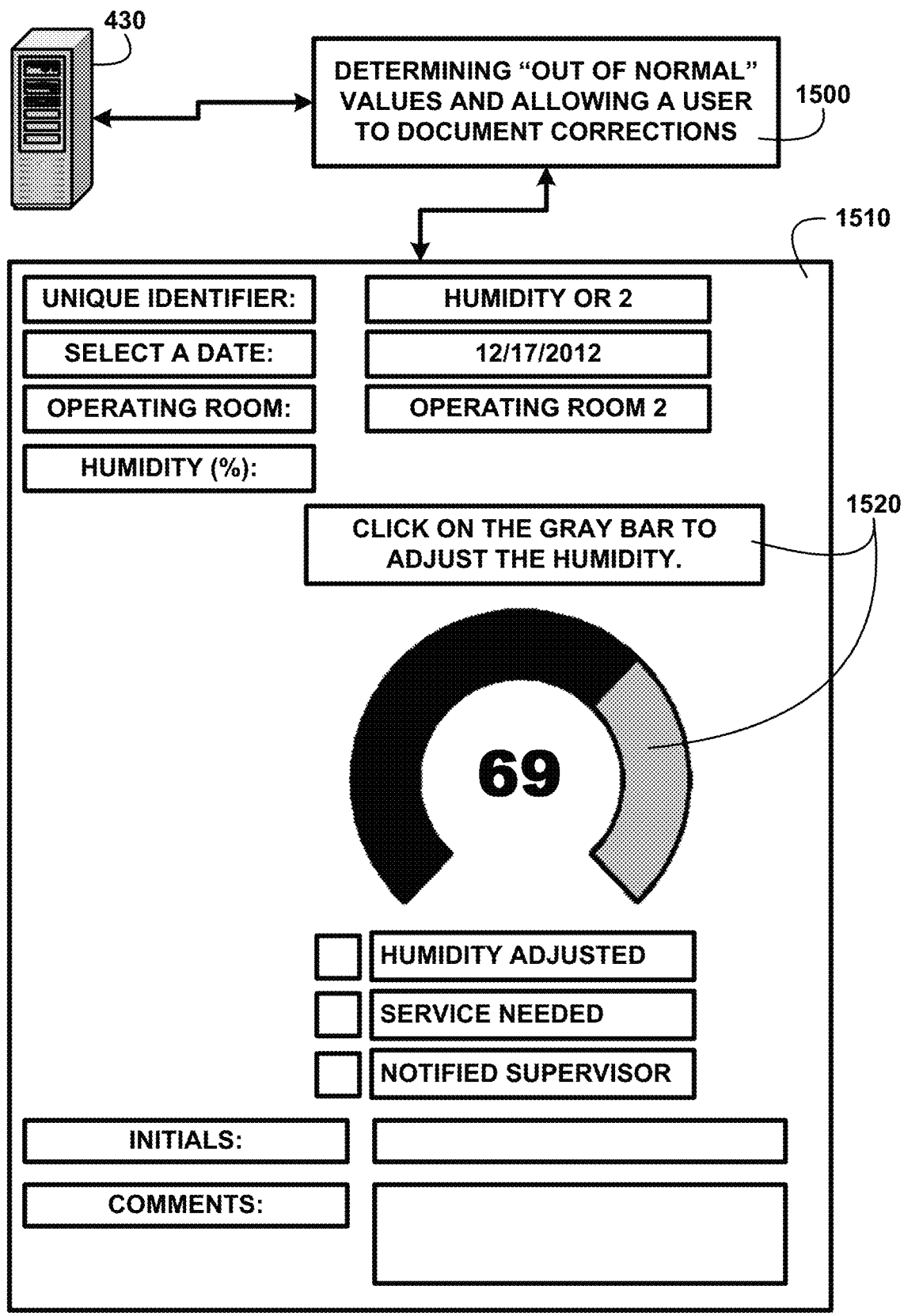
FIG. 15 shows for illustrative purposes only an example of a process to correct and document out of compliance conditions of one embodiment.

A Process to Correct and Document Out of Compliance Conditions:

FIG. 15 shows for illustrative purposes only an example of a process to correct and document out of compliance conditions of one embodiment. FIG. 15 shows the registered company server 430 determining "out of normal" values and allowing a user to document corrections 1500. In this example the display shows an out of normal condition for humidity or 2 in operating room 2 1510. The humidity sensor reading is 69% above the normal operating room compliant environmental conditions for humidity in a range of 50 to 60%.

The out of normal condition display is shown automatically to a supervisor. The display includes an instruction wherein the supervisor can click on the gray bar to adjust the humidity 1520. When the supervisor clicks on the gray bar and adjusts the humidity to become "normal" and in compliance the corrective action is recorded on the registered company server 430. Clicking on the gray bar transmits a signal to the registered company server 430 to activate a remote digital actuator including a wireless digital actuator including a wireless digital dehumidifier device humidity level setting actuator for lowering the humidity in operating room 2 to bring the humidity into compliance of one embodiment.

The foregoing has described the principles, embodiments and modes of operation of the embodiments. However, the embodiments should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. An equipment measuring and testing system for a medical facility, comprising:
   a plurality of sensors coupled to at least one medical device located in at least one operating room configured to measure operation performance levels of the medical device;
   a user interface coupled to the medical device;
   a wireless communication device coupled to each sensor of the plurality of sensors configured to wirelessly transmit the measured operation performance levels to a server;
   a database coupled to the server and configured to receive updated federal, state and private accreditation regulatory compliance limits periodically;
   at least one digital processor coupled to the server and configured to continuously compare the measured operational performance levels to the updated accreditation regulatory compliance limits to determine if the measured operational values are non-compliant and not within acceptable range values of the accreditation regulatory compliance limits or are within an acceptable range values of the accreditation regulatory compliance limits;
   a non-compliant performance value alert generated by the server when the measured operational values are non-complaint, wherein the non-compliant performance value alert is automatically transmitted to the user interface with instructions for correcting the non-compliant values; and
   a plurality of settings actuators coupled to the at least one medical device and the server and configured to automatically adjust settings of the at least one medical device to be within the acceptable range values of the accreditation regulatory compliance limits.

2. The equipment measuring and testing system for a medical facility of claim 1, wherein the predetermined range operation performance level is determined for each piece of equipment individually.

3. The equipment measuring and testing system for a medical facility of claim 1, wherein the sensor measurements are taken at predetermined interval during each day.

4. The equipment measuring and testing system for a medical facility of claim 1, wherein sensor measurements include measuring environmental conditions of areas for transmitting environmental conditions measurement data to the server on a predetermined basis.

5. The equipment measuring and testing system for a medical facility of claim 1, wherein using the server for analyzing and evaluating equipment functionality and operations performance includes at least one from a group of measurements including at least one of humidity, temperature, air flow, battery charging, voltage output, lighting levels, pressure, pixel size, x-ray beam, or electrical signals.

6. The equipment measuring and testing system for a medical facility of claim 1, further comprising a database coupled to the server configured to store settings actuator instructions.

7. The equipment measuring and testing system for a medical facility of claim 1, wherein the server is configured to include at least one processor, at least one database, and at least one wireless bidirectional communication device.

8. The equipment measuring and testing system for a medical facility of claim 1, further comprising nested thermostats and wireless digital actuators including smart devices for adjusting heating and cooling equipment devices temperature settings.

9. The equipment measuring and testing system for a medical facility of claim 1, further comprising nested thermostats and wireless digital actuators including smart devices for adjusting humidifying and dehumidifying equipment devices humidity settings.

10. The equipment measuring and testing system for a medical facility of claim 1, further comprising treatment room and operating room air flow ventilators air volume changeover measurements using an air flow cubic feet per minute (cfm) sensor are used to determine the changes wirelessly transmitted to air flow settings actuators for adjustments to meet compliance standards.

11. An equipment measuring and testing system for a medical facility, comprising:
    a plurality of sensors coupled to at least one medical device located in at least one operating room configured to measure operation performance levels of the medical device;
    wherein the sensor measurements are taken at predetermined intervals during each day;
    a user interface coupled to the medical device;
    a wireless communication device coupled to each sensor of the plurality of sensors configured to wirelessly transmit measured operation performance levels to a server;
    a server coupled to the plurality of sensors configured to determine if the at least one medical device is within the predetermined range of compliance standards and alert a user of a compliance status based on the determination;
    a database coupled to the server and configured to receive updated federal, state and private accreditation regulatory compliance limits periodically;

at least one digital processor coupled to the server and configured to continuously compare the measured operational performance levels to the updated accreditation regulatory compliance limits to determine if the measured operational values are non-compliant and not within acceptable range values of the accreditation regulatory compliance limits or are within an acceptable range values of the accreditation regulatory compliance limits;

a non-compliant performance value alert generated by the server when the measured operational values are non-complaint, wherein the non-compliant performance value alert is automatically transmitted to the user interface with instructions for correcting the non-compliant values; and a plurality of settings actuators coupled to the at least one medical device and the server and configured to automatically adjust settings of the at least one medical device to be within the acceptable range values of the accreditation regulatory compliance limits.

12. The equipment measuring and testing system for a medical facility of claim 11, wherein the predetermined operating performance ranges meeting compliance standards range levels are determined for each piece of equipment individually.

13. The equipment measuring and testing system for a medical facility of claim 11, wherein sensor measurements include measuring environmental conditions of areas for transmitting environmental conditions measurement data to the server on a predetermined basis.

14. The equipment measuring and testing system for a medical facility of claim 11, wherein using the server for analyzing and evaluating equipment functionality and operations performance includes at least one from a group of measurements including at least one of humidity, temperature, air flow, battery charging, voltage output, lighting levels, pressure, pixel size, x-ray beam, or electrical signals.

15. The equipment measuring and testing system for a medical facility of claim 11, further comprising a database coupled to the server configured to store settings actuator instructions.

16. An equipment measuring and testing system for a medical facility, comprising:
 a plurality of sensors coupled to at least one medical device located in at least one operating room configured to measure operation performance levels of the medical device;
 wherein the sensor measurements are taken at predetermined intervals during each day;
 a user interface coupled to the medical device;
 a wireless communication device coupled to each sensor of the plurality of sensors configured to wirelessly transmit measured operation performance levels to a server;
 a server coupled to the plurality of sensors configured to determine if the at least one medical device is within the predetermined range of compliance standards and alert a user of a compliance status based on the determination;
 a database coupled to the server and configured to store actuator setting instructions and to receive updated federal, state and private accreditation regulatory compliance limits periodically;
 at least one digital processor coupled to the server and configured to continuously compare the measured operational performance levels to the updated accreditation regulatory compliance limits to determine if the measured operational values are non-compliant and not within acceptable range values of the accreditation regulatory compliance limits or are within an acceptable range values of the accreditation regulatory compliance limits;
 a non-compliant performance value alert generated by the server when the measured operational values are non-complaint, wherein the non-compliant performance value alert is automatically transmitted to the user interface with instructions for correcting the non-compliant values;
 an instruction to the user to wirelessly signal the server to activate a wireless digital actuator to adjust the non-compliant medical device performance level settings for correcting the non-compliant values to bring the medical device operation into updated regulatory compliance standards and recording the corrective action on the server;
 a processor configured to perform an analytical compliance performance evaluation on the server for each medical device; and
 a plurality of settings actuators coupled to the at least one medical device and the server and configured to automatically adjust settings of the at least one medical device based on the actuator instructions to be within the acceptable range values of the accreditation regulatory compliance limits.

17. The equipment measuring and testing system for a medical facility of claim 16, further comprising nested thermostats and wireless digital actuators including smart devices for adjusting heating and cooling equipment devices temperature settings.

18. The equipment measuring and testing system for a medical facility of claim 16, further comprising nested thermostats and wireless digital actuators including smart devices for adjusting humidifying and dehumidifying equipment devices humidity settings.

19. The equipment measuring and testing system for a medical facility of claim 16, further comprising treatment room and operating room air flow ventilators air volume changeover measurements using an air flow cubic feet per minute (cfm) sensor are used to determine the changes wirelessly transmitted to air flow settings actuators for adjustments to meet compliance standards.

20. The equipment measuring and testing system for a medical facility of claim 16, wherein the server is configured to include at least one processor, at least one database, and at least one wireless bidirectional communication device.

* * * * *